(12) United States Patent
Shin et al.

(10) Patent No.: US 6,987,199 B2
(45) Date of Patent: Jan. 17, 2006

(54) PROCESS FOR PREPARING BETA-KETOESTER COMPOUND

(75) Inventors: Hyun-lk Shin, Daejeon (KR); Bo-Seung Choi, Daejeon (KR); Sang-Chul Choi, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 36 days.

(21) Appl. No.: 10/492,092

(22) PCT Filed: Oct. 14, 2002

(86) PCT No.: PCT/KR02/01918

§ 371 (c)(1),
(2), (4) Date: Apr. 9, 2004

(87) PCT Pub. No.: WO03/033469

PCT Pub. Date: Apr. 24, 2003

(65) Prior Publication Data

US 2004/0249163 A1    Dec. 9, 2004

(30) Foreign Application Priority Data

Oct. 15, 2001   (KR) ............................... 2001-63349

(51) Int. Cl.
    *C07C 67/36*   (2006.01)
    *C07D 211/70*  (2006.01)
    *C07D 211/72*  (2006.01)

(52) U.S. Cl. ...................... 560/114; 546/310; 546/315

(58) Field of Classification Search ................ 560/114; 546/310, 315
See application file for complete search history.

(56) References Cited

U.S. PATENT DOCUMENTS

| 5,204,478 A | 4/1993 | Jennings ...................... 546/315 |
| 5,380,860 A | 1/1995 | Busch et al. ................. 546/315 |

FOREIGN PATENT DOCUMENTS

| DE | 3508816 | 7/1986 |
| EP | 333020 | 9/1989 |
| KR | 1019980047902 | 9/1998 |

OTHER PUBLICATIONS

Hcaplus 107:77632, "Pyridinyl ketone derivatived", Miyamoto et. al., Apr. 14, 1986.*

* cited by examiner

*Primary Examiner*—James O. Wilson
*Assistant Examiner*—Binta Robinson
(74) *Attorney, Agent, or Firm*—Birch, Stewart, Kolasch & Birch, LLP

(57) ABSTRACT

The present invention relates to a new process for preparing beta-ketoester compound of the following formula (1), which is a useful intermediate for the synthesis of such quinoline antibiotics as Ciprofloxacin, Levofloxacin, Gemifloxacin, Trovafloxacin, etc. The quinoline antibiotics obtained from the above compound of formula (1) show potent antibacterial activity, and so are advantageously used as a therapeutic agent for bacterial infections of humans or animals.

17 Claims, No Drawings

PROCESS FOR PREPARING BETA-KETOESTER COMPOUND

TECHNICAL FIELD

The present invention relates to a new process for preparing beta-ketoester compound of the following formula (1):

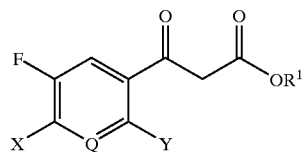

in which
R$^1$ represents C$_1$–C$_4$-alkyl or benzyl,
X and Y each represent Cl, F, or NO$_2$, and
Q represents C—H, C—F, C—NO$_2$, or N, which is a useful intermediate for the synthesis of such quinoline antibiotics as Ciprofloxacin, Levofloxacin, Gemifloxacin, Trovafloxacin, etc.

The quinoline antibiotics obtained from the above compound of formula (1) show potent antibacterial activity, and so are advantageously used as a therapeutic agent for bacterial infections of humans or animals.

BACKGROUND ART

The compound of formula (1) has been prepared through a three-step procedure as shown in the Reaction Scheme 1 below.

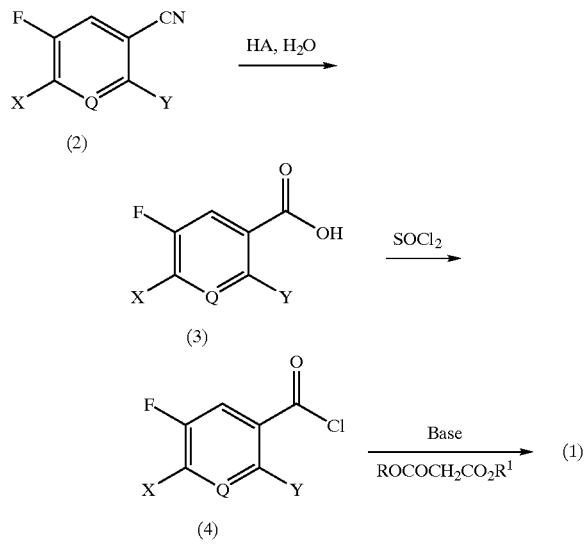

Reaction Scheme 1 in which
R$^1$, X, Y and Q are defined as above,
R represents metal, H or R$^1$, and
HA means an acid.

According to the above Reaction Scheme 1, the nitrile group of compound (2) is converted to a carboxyl group by a hydrolysis reaction (see European Patent No. 0333020 A2, 1989; U.S. Pat. No. 5,204,478, 1993), and the resulting compound (3) reacts with thionyl chloride to give acyl chloride compound (4). The compound (4) reacts with diethyl malonate and magnesium ethoxide (see *Chem. Pharm. Bull. Jpn.*, 1990, 38, 3211), or with ethyl malonic acid and n-butyl lithium (see *J. Med. Chem.*, 1986, 29, 2363), or with potassium ethyl malonate and methyl magnesium bromide, or with potassium ethyl malonate, lithium chloride and chlorotrimethylsilane (see Korean Patent Laid-open Publication No. 98-47902), or with magnesium chloride and potassium ethyl malonate (see: *J. Org. Chem.*, 1985, 50, 2622; *Synthesis.*, 1993, 290; *Org. Prep. Proc. Int.*, 1997, 29, 231; European Patent No. 0449445 A2, 1991) to produce the beta-ketoester compound (1).

DISCLOSURE OF THE INVENTION

The present inventors tried to improve the above three-step procedure and to prepare the compound of formula (1) by a more convenient and effective process. The inventors expected that the above three-step procedure can be simplified to a one-pot process if Blaise reaction (see: *J. Org. Chem.*, 1983, 48, 3833) is applied.

In the generally known Blaise reaction, however, the zinc metal used in the reaction should be activated in advance through a separate activation step. The typical activation method is a complicated process wherein the zinc metal is washed with an aqueous acid solution, filtered, washed with an organic solvent, and then dried (see: *Tetrahedron, Asymmetry,* 1998, 9, 805; J. Org. Chem., 1983, 48, 3833). Further, since the zinc metal is used in 5 to 15 times molar amount and alkyl alpha-haloacetate is used in 3 to 5 times molar amount, respectively, with respect to the starting material, a large amount of side products is generated. Therefore, it is inappropriate to apply this process to the mass production.

Thus, the present inventors extensively studied to solve the above-mentioned problems of the Blaise reaction. As a result, the present inventors have identified that if the zinc metal is activated in situ by adding a catalytic amount of organic acid or derivative thereof to the reaction solution, the complicated separate step for activating the zinc metal may be avoided and the respective amounts of zinc metal and alkyl alpha-haloacetate, used in the reaction may be reduced to an equimolar to 2.0 times molar amount with respect to the starting material with consistent reproducibility. Thus, the present invention is completed.

Therefore, it is the object of the present invention to provide an effective process for preparing the beta-ketoester compound of formula (1).

The present invention will be more specifically explained below.

BEST MODE FOR CARRYING OUT THE INVENTION

The present invention relates to a process for preparing a compound of the following formula (1):

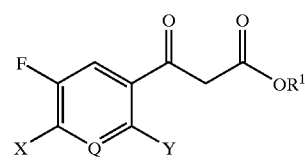

in which $R^1$, X, Y, and Q are defined as above, characterized in that a nitrile compound of the following formula (2):

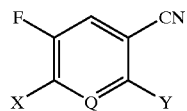

(2)

in which X, Y, and Q are defined as above, is reacted in a solvent in the presence of zinc metal and a catalytic amount of organic acid or derivative thereof with an alkyl alpha-haloacetate compound of the following formula (5):

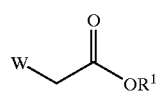

(5)

in which $R^1$ is defined as above and W represents Br or I, and then hydrolyzed in the presence of an aqueous acid solution.

The above process according to the present invention has the merits to simplify the earlier three-step preparation method to a one-pot reaction by using Blaise reaction (see *J. Org. Chem.* 1983, 48, 3833) and at the same time to enhance economic advantages through providing a consistent yield and reducing the used amounts of zinc metal and alpha-haloacetate by directly activating the zinc metal in a new manner in the reaction solution.

The present inventors have identified that the nitrile compound of formula (2) is reacted with activated zinc metal and alkyl alpha-haloacetate compound of formula (5) to form an enamino ester compound, as depicted in the following Reaction Scheme 2, and this enamino ester intermediate is treated by the aqueous acid solution to form the desired beta-ketoester compound of formula (1).

Reaction Scheme 2

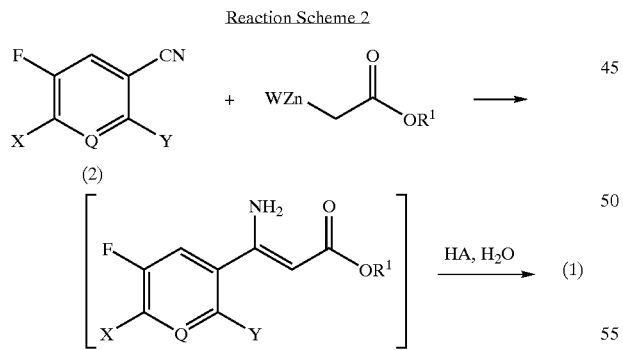

In the process of the present invention, a catalytic amount of organic acid or derivative thereof is added first into the zinc metal in a solvent, which is then stirred at reflux to activate the zinc metal. Then, the nitrile compound of formula (2) is added and subsequently the alkyl alpha-haloacetate compound of formula (5) is added dropwise. After the completion of the reaction, the resulting mixture is subjected to a hydrolysis reaction using an aqueous acid solution to give the desired compound of formula (1). The specific reaction conditions are explained in detail below.

As the solvent, one or more selected from the group consisting of tetrahydrofuran, benzene, toluene, and ether may be used. Tetrahydrofuran is the most preferable in view of purity and yield.

The alkyl alpha-haloacetate compound of formula (5) is added dropwise over 0.5 to 2 hours and the most satisfactory purity and yield are obtained when the time for the dropwise addition is in the range of 1 to 1.5 hour. It is preferable to use the compound of formula (5) in an equimolar to 2.0 times molar amount with respect to the compound of formula (2). Particularly, the compound of formula (5) wherein $R^1$ is $C_1$–$C_4$-alkyl is preferably used, and isopropyl haloacetate among them gives a better yield than methyl- or ethyl haloacetate. However, t-butyl haloacetate is better than isopropyl haloacetate.

The zinc metal is preferably used in the form of dust or powder, and preferably in an equimolar to 2.0 times molar amount with respect to the compound of formula (2). The zinc metal is stirred with the solvent at reflux generally under the temperature ranging from 60 to 120° C. As the organic acid or derivative thereof to be added to activate the zinc metal, one or more selected from the group consisting of $RCO_2H$, $RSO_3H$, $RCO_2TMS$, $RSO_3TMS$, and $(RSO_3)_2NH$ (wherein R represents hydrogen; saturated or unsaturated alkyl which has 1 to 6 carbon atoms and which is optionally substituted by halogen; or saturated or unsaturated aryl which has 6 to 12 carbon atoms and which is optionally substituted by halogen) are preferably used. The organic acid or derivative thereof is preferably used in a catalytic amount, i.e., 0.001 to 0.1 time molar amount with respect to the compound of formula (2).

In the step of hydrolysis of the enaminoester intermediate, an aqueous solution of hydrochloric acid or sulfuric acid may be used. The acid is preferably used in 2 to 5 times molar amount with respect to the compound of formula (2) in terms of purity and yield. It is preferable that the aqueous acid solution is added dropwise at temperatures ranging from 0 to 10° C. and the hydrolysis reaction is carried out at temperatures ranging from 20 to 30° C.

Particularly, a compound of the following formula (2a):

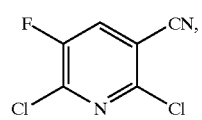

(2a)

which is the compound of formula (2) wherein X and Y each represent Cl, and Q represents N, is reacted and hydrolyzed with an aqueous acid solution to give a solid product, from which the resulting compound of the following formula (1a):

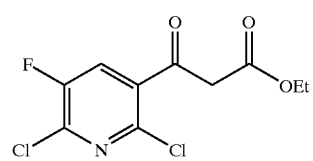

(1a)

can be obtained by simple filtering and washing procedures. Since the desired product can be purified by simple filtering and washing procedures without any further purification steps such as column chromatography that can hardly be applied to the mass production, the process is very advantageous to the industrial use. In this case, the best results are obtained to filter the product after it is allowed to stand at temperatures ranging from −5 to 10° C. and to wash the filter cake using cold (−5 to 10° C.) ethanol or a solvent mixture of ethanol and water (mixture of the ratio of 7:3 to 4:1, v/v).

Upon carrying out the reaction as explained above, the beta-ketoester compound of formula (1) can be effectively obtained from the nitrile compound of formula (2). Since the zinc metal used in the Blaise reaction according to the present invention is activated by a small amount of organic acid or derivative thereof in situ, the earlier requirement of the separate process for activating the zinc metal can be avoided. Further, the zinc metal and reactant can be used in a minimum quantity, whereby the amount of hydrogen generated from the decomposition of unreacted zinc metal during the acid hydrolysis can be reduced. Thus, the safety aspect of the reaction is improved.

Therefore, compared with the earlier process, the process according to the present invention provides a consistent yield, simple operational convenience, enhanced productivity, and the reduction of cost.

The present invention will be more specifically explained in the following examples. However, it should be understood that the following examples are intended to illustrate the present invention but not to limit the scope of the present invention in any manner.

EXAMPLE 1

Preparation of ethyl 3-(2,6-dichloro-5-fluoro-3-pyridyl)-3-oxopropanoate

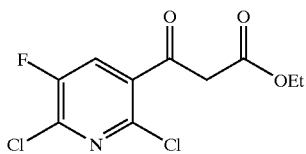

To 1.03 g of zinc dust were added 10.0. of tetrahydrofuran and 6.0 mg of methanesulfonic acid, and the mixture was stirred at reflux. To the mixture was added 2.0 g of 2,6-dichloro-5-fluoro-3-pyridylcarbonitrile, and subsequently 2.27 g of ethyl bromoacetate was added dropwise over 1 hour. After the completion of the addition, the reaction mixture was stirred at reflux for further 0.5 hour. The reaction mixture was cooled to 0 to 10° C., 10. of 3 N aqueous hydrochloric acid solution was added and the mixture was slowly warmed to room temperature. The reaction solution was stirred for 2 hours and the resulting solid was allowed to stand for 2 hours at 0 to 5° C. The solid thus obtained was filtered and washed with a solvent mixture of ethanol and water (7:3, v/v) of the same temperature to give the title compound in a yield of 78% (2.3 g).

$^1$H NMR (400 MHz, CDCl$_3$).

Enol Form (80%): 12.55 (s, 1H), 7.82 (d, J=7.6 Hz, 1H), 5.81 (s, 1H), 4.27 (q, J=7.2 Hz, 2H), 1.33 (t, J=7.2 Hz, 3H)

Keto Form (20%): 7.82 (d, J=7.6 Hz, 1H), 4.18 (q, J=7.2 Hz, 2H), 4.08 (s, 2H), 1.24 (t, J=7.2 Hz, 3H)

Mass (APCI, m/z): 278 (M−H, 43), 264 (38), 232 (24), 214 (100)

COMPARATIVE EXAMPLE 1

Preparation of ethyl 3-(2,6-dichloro-5-fluoro-3-pyridyl)-3-oxopropanoate 3.4 g of activated zinc metal and 15. of tetrahydrofuran were introduced into a reaction vessel and the mixture was stirred at reflux. To the mixture were added dropwise several drops of ethyl bromoacetate, and the mixture was stirred for 1 hour. 1 g of 2,6-dichloro-5-fluoro-3-pyridylcarbonitrile and 3.5 g of ethyl bromoacetate were slowly added dropwise over 1 hour, and then the mixture was stirred at reflux for further 30 minutes and cooled to room temperature. The reaction mixture was cooled to 0 to 10° C., 30. of 3 N aqueous hydrochloric acid solution was added, and the mixture was slowly warmed to room temperature. The reaction solution was stirred for 2 hours. After the completion of the reaction was identified by TLC, tetrahydrofuran was removed by distillation under reduced pressure. The residue was extracted with ethyl acetate and purified by silica gel column chromatography (eluent: diethylether/n-hexane=1/10, v/v) to give the title compound in a yield of 88% (1.3 g).

$^1$H NMR (400 MHz, CDCl$_3$).

Enol Form (90%): 12.55 (s, 1H), 7.82 (d, J=7.6 Hz, 1H), 5.81 (s, 1H), 4.27 (q, J=7.2 Hz, 2H), 1.33 (t, J=7.2 Hz, 3H)

Keto Form (10%): 7.82 (d, J=7.6 Hz, 1H), 4.18 (q, J=7.2 Hz, 2H), 4.08 (s, 2H), 1.24 (t, J=7.2 Hz, 3H)

Mass (APCI): 278 (M−H, 43), 264 (38), 232 (24), 214 (100)

EXAMPLE 2

Preparation of ethyl 2,4,5-trifluorobenzoylacetate

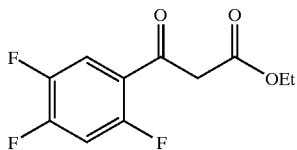

To a stirred suspension of 125 mg of zinc dust in 5.0. of tetrahydrofuran was added 11.0 mg of methanesulfonic acid and the mixture was heated at reflux. To the mixture was added 200 mg of 2,4,5-trifluorobenzonitrile, and subsequently 276 mg of ethyl bromoacetate was added dropwise over 1 hour. After the completion of the addition, the mixture was stirred at reflux for further 0.5 hour. The reaction mixture was cooled to 0 to 10° C., 1. of 3N aqueous hydrochloric acid solution was added, and the mixture was slowly warmed to room temperature. The reaction solution was stirred for 2 hours. Tetrahydrofuran was removed by distillation under reduced pressure. The residue was extracted with ethyl acetate and purified by silica gel column chromatography (eluent: ethylacetate/n-hexane=1/10, v/v) to give the title compound in a yield of 80% (250 mg).

$^1$H NMR (400 MHz, CDCl$_3$).

Enol Form (75%): 12.15 (s, 1H), 7.47 (q, J=7.8 Hz, 1H), 7.04 (q, J=7.8 Hz, 1H), 5.91 (s, 1H), 4.26 (q, J=7.2 Hz, 2H), 1.32 (t, J=7.2 Hz, 3H)

Keto Form (25%): 7.66 (q, J=7.8 Hz, 1H), 7.04 (q, J=7.8 Hz, 1H), 4.16 (q, J=7.2 Hz, 2H), 4.10 (s, 2H), 1.21 (t, J=7.2 Hz, 3H)

Mass (FAB, m/z): 247 (M+H)

INDUSTRIAL APPLICABILITY

The new one-pot process for the preparation of the compound of formula (1) is superior to the reported three-step procedure in terms of the consistent yield, the enhanced productivity, and the reduced production cost.

What is claimed is:

1. A process for preparing a compound of the following formula (1):

<img alt="formula 1" />  (1)

in which
R$^1$ represents C$_1$–C$_4$-alkyl or benzyl,
X and Y each represent Cl, F, or NO$_2$, and
Q represents C—H, C—F, C—NO$_2$, or N, characterized in that a nitrile compound of the following formula (2):

<img alt="formula 2" />  (2)

in which X, Y, and Q are defined as above, is reacted in a solvent in the presence of zinc metal and a catalytic amount of organic acid or derivative thereof with an alkyl alpha-haloacetate compound of the following formula (5):

<img alt="formula 5" />  (5)

in which R$^1$ is defined as above and W represents Br or I, and then hydrolyzed in the presence of an aqueous acid solution.

2. The process according to claim 1 which proceeds as a one-pot reaction.

3. The process according to claim 1 wherein the solvent is one or more selected from the group consisting of tetrahydrofuran, benzene, toluene, and ether.

4. The process according to claim 3 wherein the solvent is tetrahydrofuran.

5. The process according to anyone of claims 1 to 4 wherein R$^1$ represents C$_1$–C$_4$-alkyl in the alkyl alpha-haloacetate compound of formula (5).

6. The process according to claim 5 wherein the alkyl alpha-haloacetate compound of formula (5) is used in an equimolar to 2.0 times molar amount with respect to the compound of formula (2).

7. The process according to claim 1 wherein the zinc metal is used in an equimolar to 2.0 times molar amount with respect to the compound of formula (2).

8. The process according to claim 1 or 7 wherein the zinc metal is in the form of dust or powder.

9. The process according to claim 1 wherein the organic acid or derivative thereof is one or more selected from the group consisting of RCO$_2$H, RSO$_3$H, RCO$_2$(trimethylsilyl) TMS, RSO$_3$TMS, and (RSO$_3$)$_2$NH, wherein R represents hydrogen; saturated or unsaturated alkyl which has 1 to 6 carbon atoms and which is optionally substituted by halogen; or saturated or unsaturated aryl which has 6 to 12 carbon atoms and which is optionally substituted by halogen.

10. The process according to claim 1 or 9, the organic acid or derivative thereof is used in a catalytic amount of 0.001 to 0.1 time molar amount with respect to the compound of formula (2).

11. The process according to claim 1 wherein the aqueous acid solution is aqueous hydrochloric acid solution or aqueous sulfuric acid solution.

12. The process according to claim 11 wherein the aqueous acid solution is aqueous hydrochloric acid solution.

13. The process according to claim 11 wherein the acid is used in 2 to 5 times molar amount with respect to the compound of formula (2).

14. The process according to claim 11 wherein the aqueous acid solution is added dropwise at temperatures ranging from 0 to 10° C. and the hydrolysis reaction is carried out at temperatures ranging from 20 to 30° C.

15. The process according to claim 1 wherein a compound of the following formula (2a):

<img alt="formula 2a" />  (2a)

which is the compound of formula (2) wherein X and Y each represent Cl, and Q represents N, is reacted and hydrolyzed to give a solid product, which is then filtered and washed to give a compound of the following formula (1a):

<img alt="formula 1a" />  (1a)

16. The process according to claim 15 wherein the washing is carried out using ethanol or a solvent mixture of ethanol and water.

17. The process according to claim 16 wherein the mixing ratio of the solvent mixture of ethanol and water is 7:3 to 4:1 (v/v).

* * * * *